United States Patent [19]
Ivey, Jr.

[11] Patent Number: 6,053,738
[45] Date of Patent: Apr. 25, 2000

[54] SENSE-SIMILE TRANSMISSION MACHINE

[76] Inventor: Ellwood G. Ivey, Jr., 1730 E. 33rd St., Savannah, Ga. 31404

[21] Appl. No.: 09/252,052

[22] Filed: Feb. 17, 1999

[51] Int. Cl.⁷ .................................................. G09B 19/00
[52] U.S. Cl. ......................... 434/127; 434/433; 273/460
[58] Field of Search ................. 434/127, 66, 37, 434/377; 273/460

[56]     References Cited
U.S. PATENT DOCUMENTS

| | | | |
|---|---|---|---|
| 4,952,400 | 8/1990 | Tararuj et al. | 424/401 |
| 5,018,974 | 5/1991 | Carnahan et al. | 434/98 |
| 5,626,155 | 5/1997 | Saute | 132/200 |
| 5,640,931 | 6/1997 | Markham | 119/711 |
| 5,797,353 | 8/1998 | Leopold | 119/710 |

*Primary Examiner*—Robert A. Hafer
*Assistant Examiner*—Bena B. Miller
*Attorney, Agent, or Firm*—John L. James

[57]     ABSTRACT

A sensualizer or sense-simile machine reproduces smells and flavors using a cylinder housing smell and flavor cartridges. A texture chamber replicates textures that stimulate the sense of touch through the fingers. Environmental conditions are replicated in a weather chamber. The machine can be activated from a remote location over a standard telephone line or accessed through a computer over a modem. With a computer or other input device, simulations and reproductions can be done locally.

10 Claims, 9 Drawing Sheets

```
        TEXTURE
    □      WOOL
    □      COTTON
    □      SILK
```

*FIG. 17*

```
        WEATHER
    □      RAIN
    □      HEAT
    □      FOG
    □      WIND
```

*FIG. 18*

```
    □      TIMES
    □      PROPERTIES
    □      CONTROL
    □      CANCEL
    □      OK
```

*FIG. 19*

FRAGRANCE/
NOSE

FIG. 20

TASTE/
TONGUE

FIG. 21

ENVIRO-FEEL

FIG. 22

TEXTURE/
TOUCH

FIG. 23

SENSE-SIMILE TRANSMISSION MACHINE

CROSS-REFERENCE TO DISCLOSURE DOCUMENT

This application of the inventor is based on his Disclosure Document No. 414,639, filed Feb. 20, 1997, entitled Sense-Simile Transmission Machine—Senx Machine.

This application is related to co-filed application Ser. No. 09/252,051, filed on even date herewith by Ellwood G. Ivey, Jr. entitled Sense-Simile Transmission Machine.

FIELD OF THE INVENTION

The present invention relates generally to an information transmitting and receiving device, and, more particularly, to a device for transmitting and receiving sensory information.

BACKGROUND OF THE INVENTION

People receive and react to stimuli using the senses of sight, touch, taste, smell and hearing. Technological advancements, especially television and computers, bring information into the home or office making it convenient for a person to partially experience a particular environment, event or thing. Unfortunately, television and computers only provide stimuli for sight and hearing leaving taste, smell and touch to the imagination or past experience. Accordingly, it will be appreciated that it would be highly desirable to have a device that provides stimuli for the senses of taste, smell and touch so that a person can totally experience a particular environment, event or thing.

SUMMARY OF THE INVENTION

Briefly summarized, according to one aspect of the present invention, an apparatus comprises a housing, smell replicating apparatus in the housing for replicating desired smells, taste replicating apparatus in the housing for replicating desired tastes, touch replicating apparatus for replicating desired feels, texture simulating apparatus for simulating desired textures, and environmental condition simulating apparatus for simulating desired environmental conditions.

When combined in predetermined proportions, the smell and flavor substances from the cartridges replicate a particular smell or flavor. The machine can be used as a stand alone unit or as a computer peripheral like a facsimile machine. It is most powerful when used with a computer on the internet because the computer visuals can be enhanced with smells, tastes, textures for the fingers to feel and weather conditions.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE PREFERRED EMBODIMENTS

The present invention is a sensualizer or sense-simile machine that facilitates the virtual transmission of flavors, smells, material textures and environment conditions from one location to another over a standard communications link, such as a telephone line, for example. At the transmitting end of the line, the user inputs data representative of the sense information to be transmitted. For example, a restaurant may want to communicate the smell and taste of a particular item. The restaurant inputs information pertaining to the smell and flavor of the item according to predetermined parameters for the particular smell or flavor. This is easily done via a computer program once the smells and flavors have been identified and quantified. The restaurant transmits the code which arrives at the receiver into a receiving unit that deciphers the code and causes the machine to emit the corresponding odor and the corresponding flavor or other conditions that have been transmitted. When used for internet shopping, a receiving unit is connected to a computer which accesses a particular merchant. In the case of a restaurant, its web site will contain pictures of various food icons along with their sense-simile codes. A transmission occurs when the particular food item is clicked on the screen or the coded information is input via the computer keyboard to activate the sense-simile machine to produce the aroma and taste connected with the food.

Figure 1:
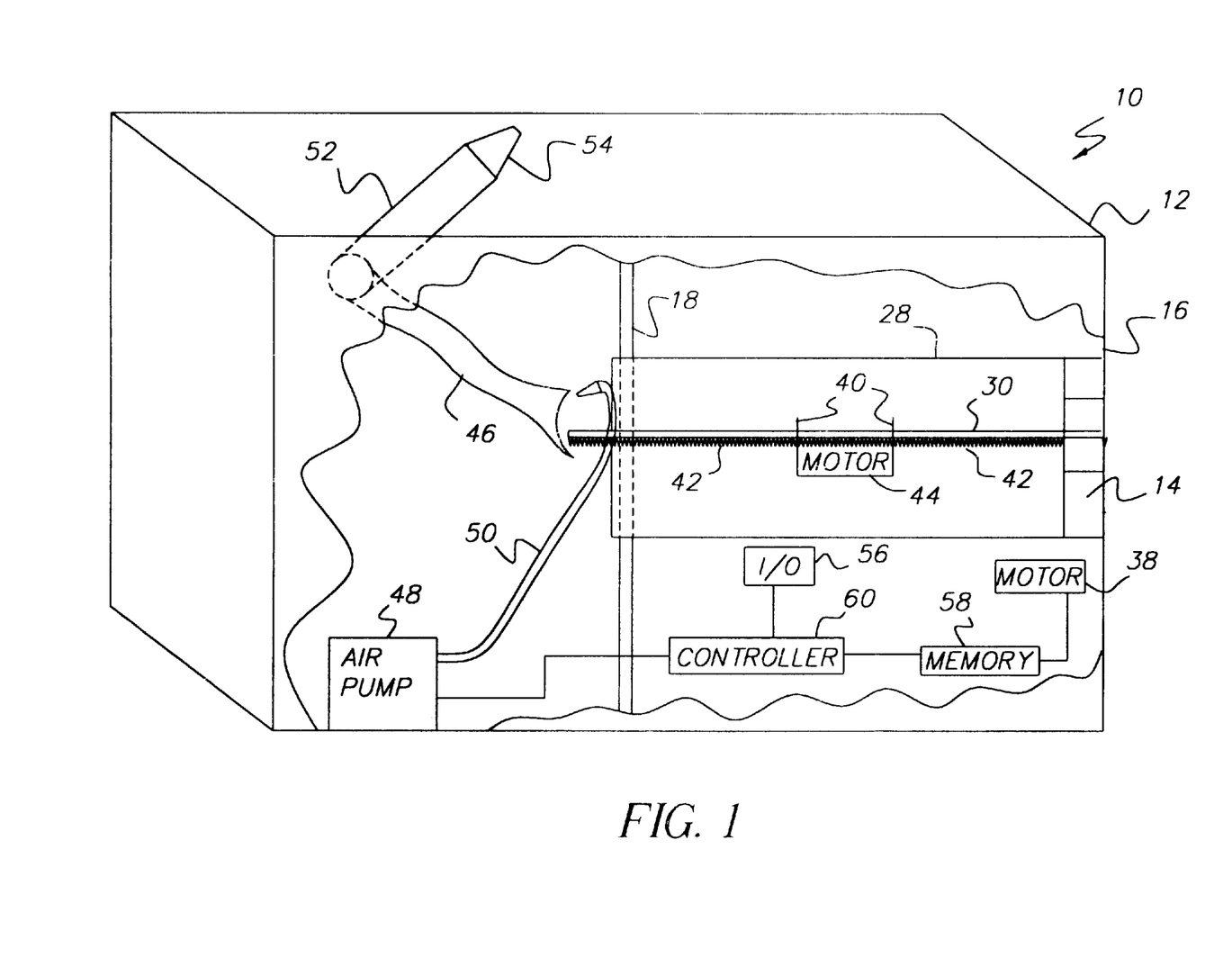
FIG. 1 is a diagrammatic perspective view with portions cut away of a preferred embodiment of a sense-simile 10 according to the present invention.

Referring to FIG. 1, a sense-simile machine 10 is configured in the form of a box that is a housing for the components of the machine. The housing 12 has left and right sidewalls, top and bottom walls, a rear wall and a front wall. The front wall is shown cut away to reveal the internal parts of the machine. A mounting bracket 14 is attached to the right sidewall 16 and a second mounting bracket 18 is spaced from the first mounting bracket 14 and attached to the top and bottom walls of housing 12. A cylinder 28 and an elongated mounting rod 30 are connected to the first mounting bracket 14 that is attached to the right sidewall 16. Additional support for cylinder 28 is provided at the left end of the cylinder by the second mounting bracket 18. The elongated mounting rod 30 extends along the longitudinal axis of cylinder 28.

Figure 2:
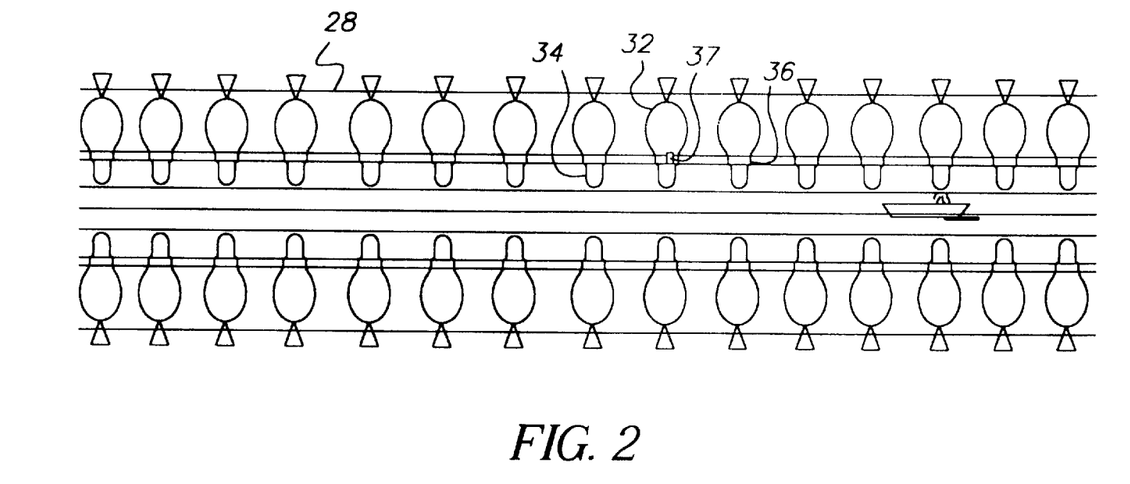
FIG. 2 is a diagrammatic sectional view of a sense cylinder for the sense-simile machine of FIG. 1.

Referring to FIGS. 1 and 2, cylinder 28 has a plurality of cavities arranged in rows with each cavity adapted to receive a cartridge 32 containing a substance, such as a liquid or powder odorous substance. Each cartridge 32 has an outlet 34 for dispensing the substance contained therein. The outlet is preferably controlled by a piezoelectric transducer 36 which opens the outlet 34 to dispense a predetermined amount of the substance contained therein. Where the odorous substance is a liquid each operation of the piezoelectric transducer 36 allows one drop of the liquid to be dispensed. Each cartridge contains a different odorous substance that is dispensed one drop at a time. By combining different numbers of drops of different substances, a particular smell is created by the drops of substances to reproduce a desired aroma. When a cartridge is emptied it can be replaced individually without the necessity of replacing all of the cartridges.

An infrared sensor 37 is housed juxtaposed to piezoelectric transducer 36 to monitor the cartridge content. When the content reaches about eighty percent depletion, sensor 37 signals controller 60 which is programmed to automatically access the cartridge supplier to place an order for a new cartridge.

Cylinder 28 is rotatable about its longitudinal axis by a motor 38. Motor 38 is preferably a stepper motor which steps the cylinder 28 enough steps to rotate the cylinder one-eighth of a revolution during each stepping operation. Each operation of motor 38 then brings a new row of cartridges to the top position on the cylinder for dispensing downward under the force of gravity. The dispensed substance is collected on a carrier 40 mounting on the mounting rod 30 and is adapted to reciprocate within cylinder 28 from one cartridge to another to collect predetermined amounts of the substances from each selected cartridge. Preferably, mounting rod 30 has a plurality of teeth 42 and a stepper motor 44 has a shaft with teeth or other mechanism adapted to engage the teeth on the mounting rod to move carrier 40 along the rod in discrete steps so that carrier 40 can be positioned precisely underneath a selected one of the cartridges 32. The cartridges 32 are activated by a piezoelectric transducer 36 of the extensional type in which motion is generated by applying a voltage to the piezoelectric crystal in a radial direction. Stepper motors 38 and 44 can operate in both the forward and reverse directions so that cylinder 28 can be rotated both clockwise and counterclockwise to position the precise row at the top, and carrier 40 can be moved both to the left and to the right to precisely position it underneath the desired cartridge.

The substance collected on the carrier is dispersed by moving the carrier to the end of the mounting rod 30 which is at the left end of the cylinder 28 as viewed in FIG. 1. At this position, carrier 40 is at the mouth of a collection tube 46 and is in the path of an accelerating means such as air pump 48 and pump outlet tube 50. Where space and energy must be conserved, air pump 48 can be replaced with a compressed air canister to provide a blast of pressurized air to accelerate the odor substance into the mount of collecting tube 46. Collection tube 46 has one end attached inside the housing about the top wall, front wall or sidewall which has an opening for tube 46. The other end of tube 46 is positioned at the left end of the cylinder to receive the substance when the air blast from the pump 48 forces the substance from the carrier 40 into the mouth of tube 46. A moveable arm 52 is attached outside of housing 12 to the top wall, sidewall or front wall about the opening where tube 46 is attached, thereby forming a fluid pathway from the collection tube 46. Moveable arm 52 is pivotal about the opening and is preferably an extension type arm that can be pivoted or swiveled to a desired position to place a nozzle 54 at a convenient location for smelling the odor to be emitted from nozzle 54. The odor abounds as the substance is dispensed through nozzle 54.

The machine also preferably includes input means 56 for inputting information regarding the amount of each substance to be deposited on the carrier. Memory 58 stores position data for the carrier and cylinder and stores position and content data for each of the cartridges. At any given moment it is known the contents of each cartridge and the amount of substance in the cartridge. A controller 60 connected to the memory means and input means receives input data from input means 56, such as a computer keyboard for example, or a communications line. The controller determines travel distances and travel directions for both the carrier and the cylinder. By knowing the exact position of these at all times, controller and the memory are able to calculate the number of steps required to move the carrier and the cylinder for extracting a given number of drops or specific amount of substance from a given cartridge. The controller causes the carrier to pause under a selected cartridge according to the input information and the controller emits a signal that causes selected cartridges to release a measured amount of the substances by causing the piezoelectric transducers with the cartridge to release a measured amount of substance.

Instead of having its own central processing unit comprised of the controller, memory and input/output unit, the machine may use a personal computer's processor and memory and be connected to the computer as printers and other peripherals are connected. This construction would reduce the cost and complexity of the sense-simile machine when integrated with the computer like other peripherals.

Figure 3:
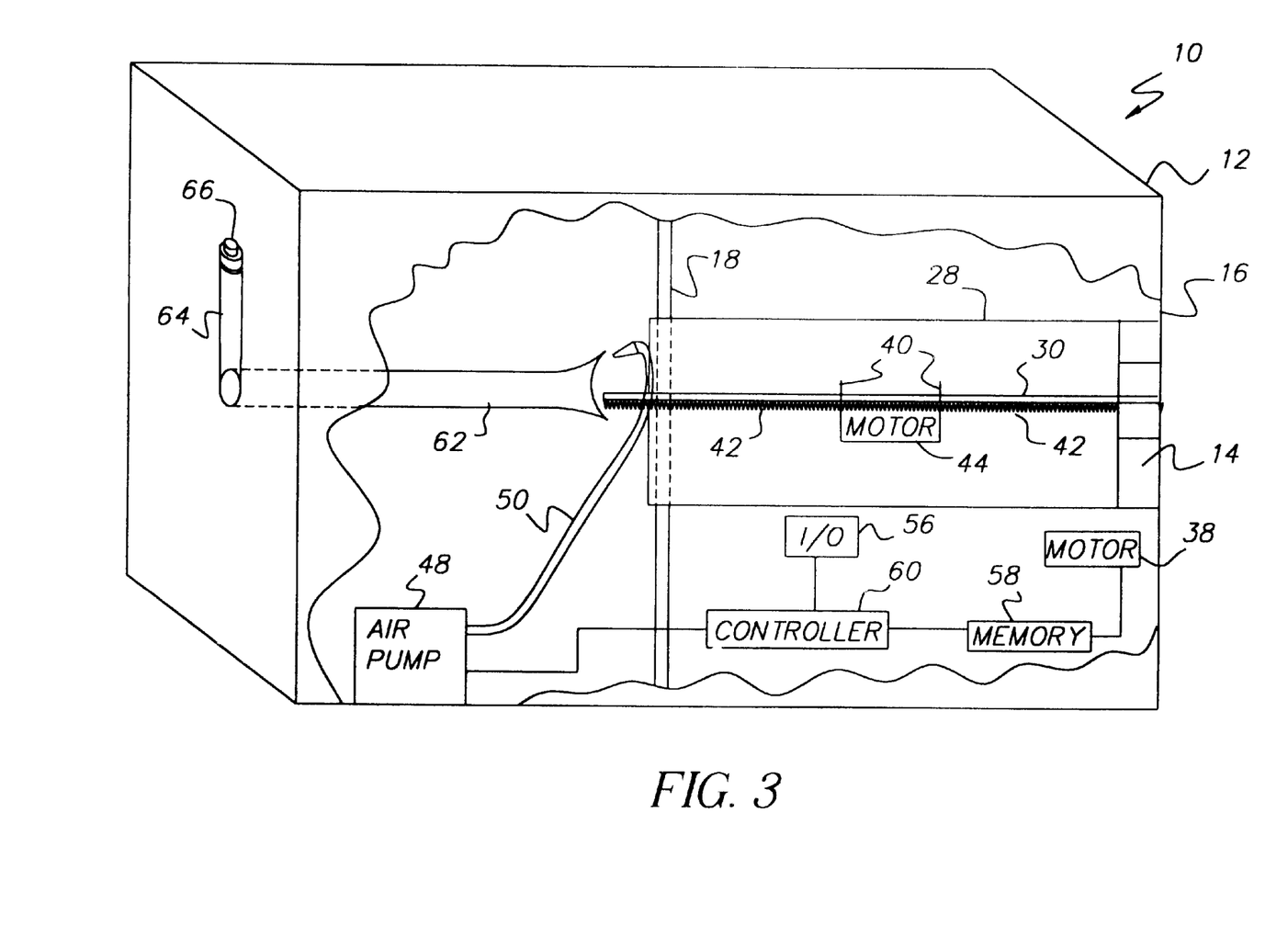
FIG. 3 is a sense-simile machine similar to FIG. 1 but illustrating another preferred embodiment.

Referring to FIG. 3, the sense-simile machine illustrated is similar to the machine of FIG. 1 but is adapted for taste instead of smell. This machine has a collection tube 62 through which a flavor or taste substance travels when it is accelerated from the carrier. It travels through an opening illustrated on the left sidewall of the housing through a hollow dispensing arm 64 that has a holder 66 on its open end for a wafer. The wafer is an edible wafer that absorbs the flavor or taste substance that is accelerated through the tube 62 and arm 64. The wafer is removed from holder 64 and eaten. The wafer acquires the taste of the substance and its smell. This embodiment of the invention thus improves over the simple smell function by adding taste or flavor which is a combination of taste and smell. A cartridge for the machine is either a smell cartridge or a taste cartridge and where both taste and smell are desired a machine may be equipped with a smell cylinder and a taste cylinder. The flavors and smells are available from Flavor and Fragrance Specialties, 300-T Corporate Drive, Mahwah, N.J. 07430.

Figure 4:
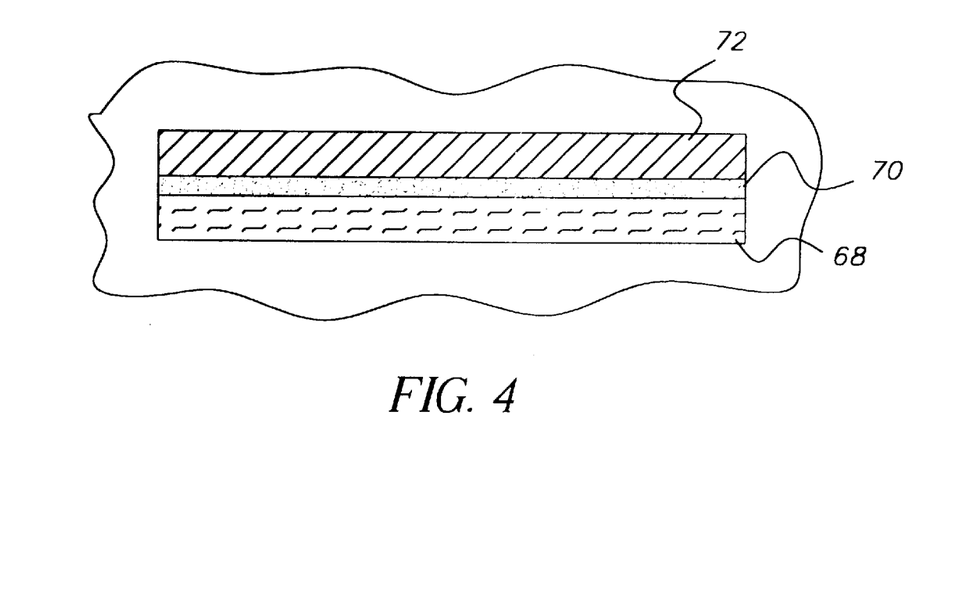
FIG. 4 illustrates a sense-simile machine wherein the cartridge is a solid simulator.

FIG. 4 illustrates a sense-simile machine wherein the cartridge is a texture simulator. It has semi-permeable membrane acting as a substrate that conducts impulses affixed to a conductive polymer fiber 72 through a conductive syndesis region 70. Conductive polymer fiber 72 has hair-like structures that stimulate the nerves in human fingers The membrane 68 and syndesis region 70 transforms the fiber's structure to simulate a desired texture by passing an electric current across the region. An opening in the top front or sidewall of the housing provides access to the texture simulator.

Figure 5:
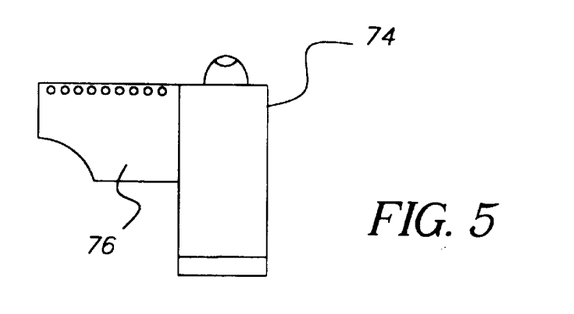
FIGS. 5 and 6 illustrate a sense-simile machine employing a texture cartridge for simulating textures.
Figure 6:
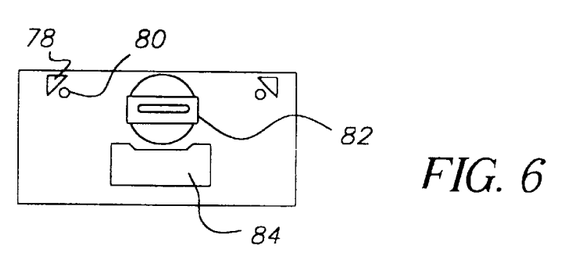

Referring to FIGS. 5 and 6, touch may also be achieved by using a texture cartridge 74. The cartridge contains samples of fabrics 76 on a 35 mm film type spool. The samples are neutral in color to allow for the samples to be illuminated by halogen lamps 78 positioned in the side and upper fold. There are colored lenses 80 that rotate in front of the lamps to provide multiple colors and textures to be illuminated onto the fabric samples. The face of the texture of the viewing area has a clear plastic 82 covering the fabric. Immediately beneath the viewing area is a slit 84 on the face of the machine allowing a human hand to enter and actually feel the fabric. The controller will operate a motor or other device that will advance the fabric samples according to the input information until the desired fabric is at the viewing area. By this construction, the sense-simile provides fabric samples that can be felt with the hand and also provides a color indication visible with the eye to simulate a desired material. This machine would allow somebody at a remote location to transmit information that would help someone choose fabrics for draperies or other decorations without ever leaving home.

Figure 7:
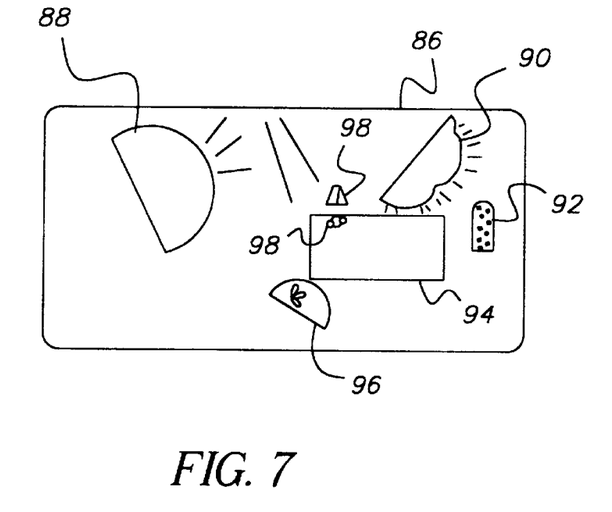
FIG. 7 illustrates a sense-simile machine employing an environment cartridge to simulate environmental conditions.

Referring to FIG. 7, an environment cartridge 86 houses a heating lamp 88 and cooling agent 90 for rapid production of desired temperature. Cooling agent 90 may be a container of compressed gas which cools as it expands rapidly when leaving the canister, or the cooling agent may be a chemical that absorbs heat when activated. A liquid capsule 92 is also housed in the cartridge to provide humidity in chamber 94. Housed in the machine behind the cartridge slot is a fan 96 and a low power laser 98. Fan 96 simulates wind velocity while heating lamp 2 and cooling agent 90 control the temperature. An oval rotating lens 98 with apertures placed in front of the low power laser 98 simulates raindrops on the human skin. The slower the revolution of the lens, the heavier the drops, conversely the faster the rotation the lighter the raindrops.

It can now be appreciated that a sense-simile machine has been presented that uses flavor and fragrance cartridges. The cartridges are removable from the cylinder and replaceable. Refillable cartridges can also be used. The cylinders themselves in one configuration of the invention are cylindrical with a round cross section and are about ten inches in length and eight and a half inches in circumference. The cylinder attaches to the right sidewall of the housing. The detaching mechanism is octagonal in configuration which allows the cylinder to turn in eighths of a revolution. The kernel shaped cylinders house either synthetic flavors or fragrances and are replaceable but not necessarily interchangeable between cylinders. They are housed in the cylinders like kernels of corn are arranged on a cob, from the outer part to the inner part. The inner point of the kernel cartridge releases the fragrance or flavor upon command into the carrier trough which is affixed to the center mounting rod. The carrier moves back and forth upon command along the rod like the print head in a printer. The carrier is sprayed via the selected fragrance or flavor kernel which rotates in eighths to the upright position to release its content. The carrier then travels to the blast tube zone at the left end of the cylinder. After the contents of the carrier are dispersed, an extra blast of air will remove any remaining residue from the passageway to prevent build-up of substance in the passageways and prevent improper mixing of flavors and fragrances.

As an alternative to the single use of holder 66 to hold a wafer, wafer holder 66 can be removed allowing the flavor to be dispersed as a mist by the user attaching a personal straw into dispensing arm 64.

As an alternative to the single use carrier, the carrier can be used to hold a wafer trough on one side and a mist trough on the other side. The selected trough is rotated to the top position so that it can collect the substance dispensed from the cartridges.

Figure 8:
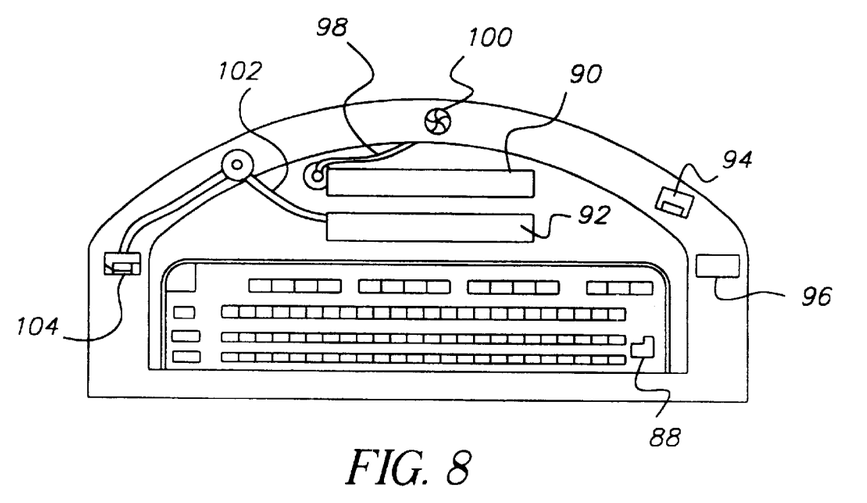
FIG. 8 illustrates a sense-simile machine incorporated with a standard computer keyboard.

The four functions described above may be combined into one unit having capability of providing fragrances, flavors, textures, and environment. For example, FIG. 8 illustrates the sense-simile machine incorporated with a standard computer keyboard. It is configured so that it fits about a keyboard 88. It incorporates a fragrance cylinder 90, a flavor cylinder 92, a texture chamber 94, and an environmental chamber 96. Smells travel along collecting tube 98 and are emitted through an aperture 100 while flavors travel through a collecting tube 102 to collect on a wafer held in moveable arm 104.

Figure 9:
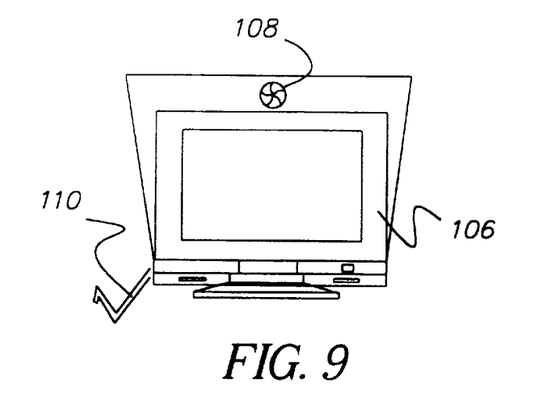
FIG. 9 illustrates a sense-simile machine incorporated about a computer monitor.

FIG. 9 illustrates the sense-simile machine constructed about a computer monitor 106. An aperture 108 for emitting smells is located above the top of the screen while the wafer holding arm 110 is to the left of the computer screen near the bottom. Openings for the environment chamber and the solid simulator may be placed on either side or on the top.

Figure 10:
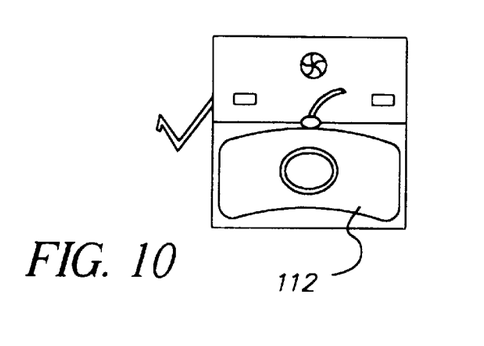
FIG. 10 illustrates a sense-simile machine incorporated with a mouse pad.
Figure 11:
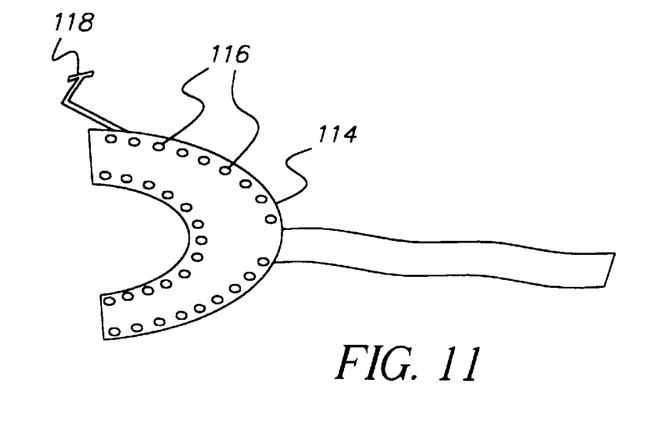
FIG. 11 is a sense-simile collar that is worn around a user's neck for virtual reality experiences.

FIG. 10 illustrates the machine incorporated with a mouse pad 112. FIG. 11 is a collar 114 that is worn around a user's neck for virtual reality experiences. For example, if the virtual participant is walking through a flower garden in spring, the embedded commands in the virtual collar would automatically produce and send the flower fragrance and air temperature to simulate the virtual reality scene. The collar has apertures 116 for emitting the smells and a wafer holding arm 118 for holding the wafer that will absorb the flavors.

Figure 12:
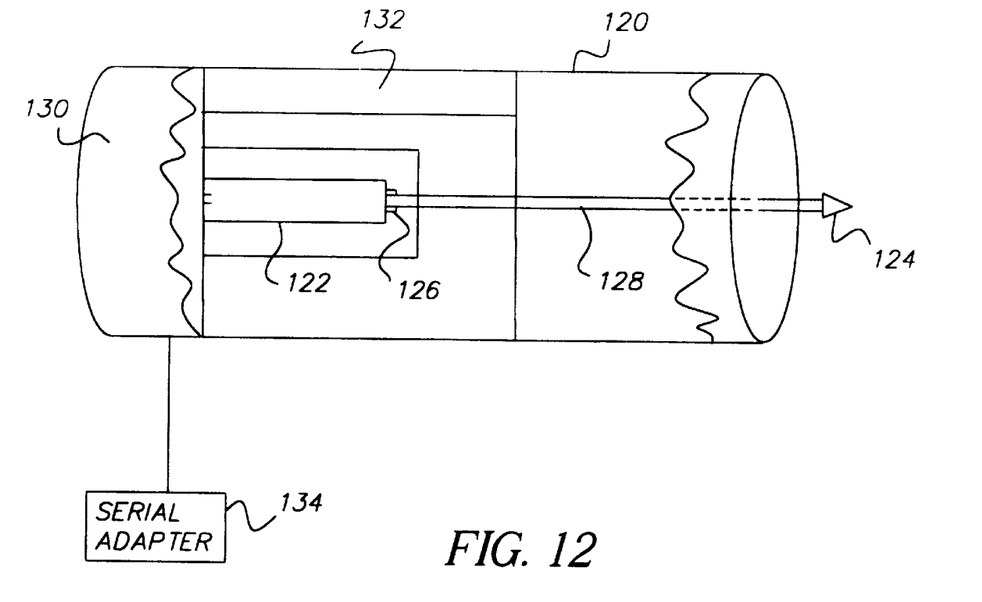
FIG. 12 illustrates a miniature sense simile machine.

FIG. 12 illustrates a sense simile sampler 120 which is a miniature Senx™ machine to be used as a give away or promotional item. It has a cylindrical housing containing a pre-mixed flavor or fragrance cartridge 122 that emits the flavor or smell substance through a nozzle 124. A piezoelectric transducer 126 opens cartridge 122 so that the substance can travel through tube 128 to nozzle 124. An air pump or compressed air unit 130 provides the force to push the substance out of cartridge 122 through tube 128 to nozzle 124. Operation is managed by a controller 132 that receives input from a computer through a serial adapter 134. This miniature machine is approximately six inches in length and three and a half inches in girth. A user visits the web site of the sample provider and clicks on the designated icon. The cartridge preferably provides two samples and is used in conjunction with viewing information on the computer. Afterwards, the miniature machine is returned or otherwise recycled.

Figure 13:
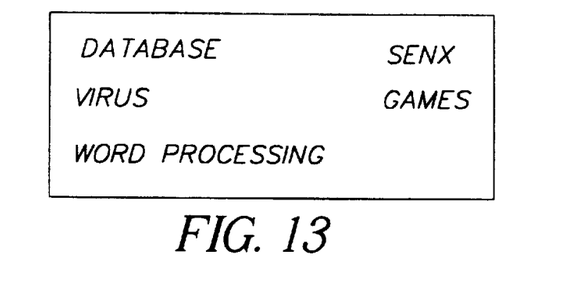
FIG. 13 illustrates a computer screen for accessing a program to operate a sense-simile machine.
Figure 14:
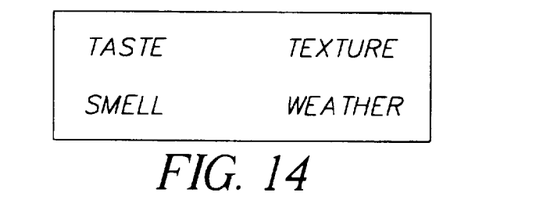
FIG. 14 illustrates selections available when the Senx™ icon is selected on the computer screen of FIG. 13.
Figure 15:
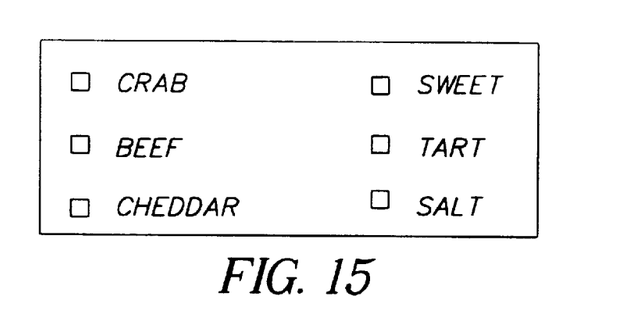
FIG. 15 illustrates further selections when taste is selected.
Figure 16:
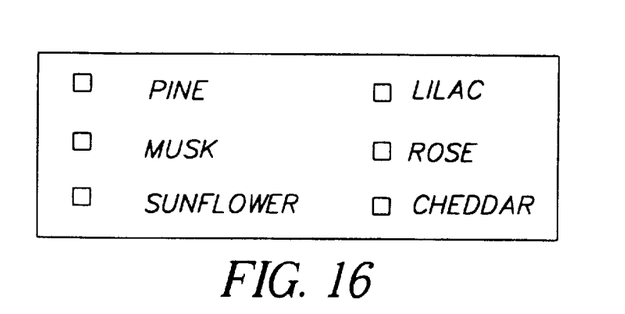
FIG. 16 illustrates selections of smells available.
Figure 17:
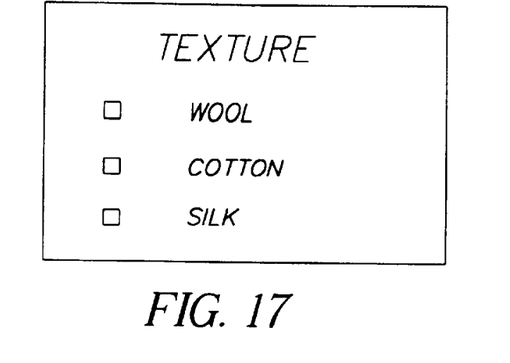
FIG. 17 illustrates available selections of textures.
Figure 18:
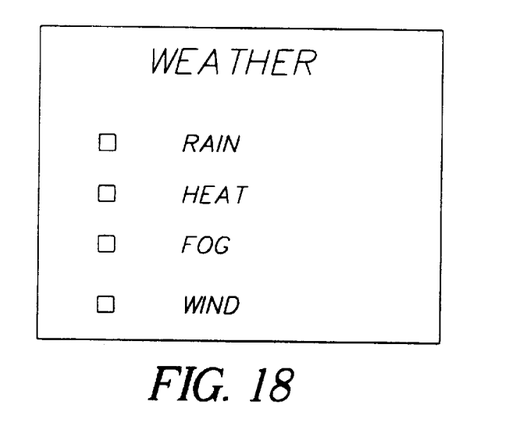
FIG. 18 illustrates available weather selections.
Figure 19:
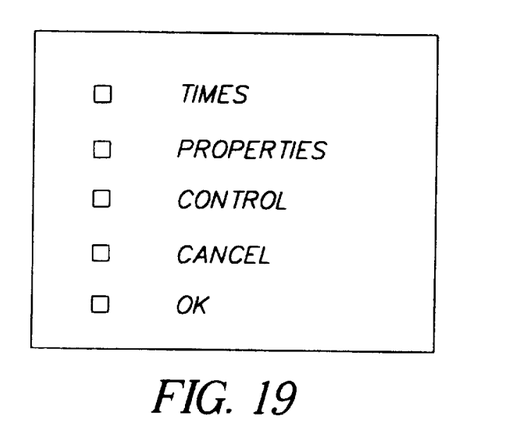
FIG. 19 illustrates other selections available.

The sense-simile machine may be operated from the computer desktop like other peripherals. The Senx™ program is clicked using the mouse on the computer screen as illustrated in FIG. 13. FIG. 14 shows the choices available when the Senx™ program is accessed. The choices are taste, texture, smell and weather. FIG. 15 shows further selections when taste is selected. You may choose from a list of available tastes. Similarly, FIG. 16 shows the choices of smells available. FIG. 17 shows the available choice of textures while FIG. 18 shows the weather choices. When taste, smell, texture or weather are chosen there is always the option of inputting a code for a particular combination if the code is known. Once the selection is made, other choices are made as illustrated in FIG. 19. These choices include times which indicate the number of releases; that is, the number of times that particular combination of smells or flavors is released onto the carrier which will determine the intensity of the smell or flavor. NUMBER OF TIMES pertains to the smell and taste functions of the machine. Similarly, PROPERTIES refers to the touch and environment functions determining release characteristics such as heavy, medium, light, or mist for various conditions. The CONTROL function tells when a cartridge needs changing or maintenance is required. The CANCEL function aborts previous commands. The OK command means proceed as selected. These functions are used to send commands to a remote unit or to operate a sense machine connected to the computer.

Figure 20:
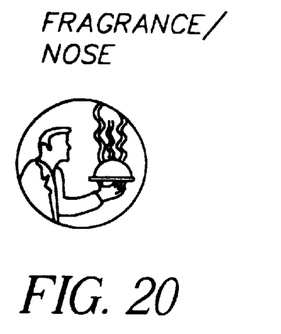
FIG. 20 illustrates an icon for smell.
Figure 21:
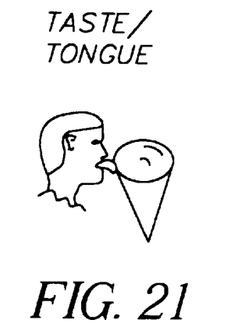
FIG. 21 illustrates an icon for taste.
Figure 22:
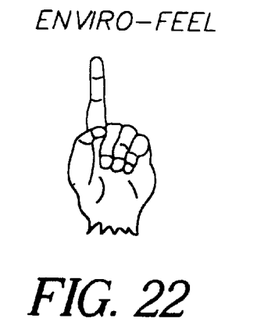
FIG. 22 illustrates an icon for environment.
Figure 23:
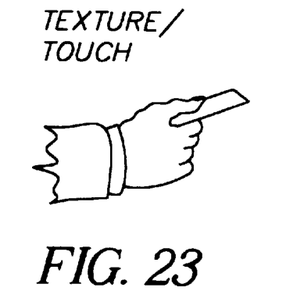
FIG. 23 illustrates an icon for texture.

FIGS. 20 through 23 show various icons that may be used on the screen. FIG. 20 illustrates a person holding a dish with aromatic vapors exuding from the dish which is used as an icon for smell. FIG. 21 illustrates a person with the tongue licking an ice cream cone which is used as an icon for taste. FIG. 22 illustrates a hand with the index finger extended as if to sensitively touch which is used as an icon for environment. FIG. 23 illustrates a hand with the thumb an index finger grasping a piece of material as if to inspect the material by rubbing it between the fingers which is used as an icon for texture.

In the present invention, a jet delivery system is provided which delivers synthetic flavors and fragrances by expelling droplets of a liquid or powdered synthetic material from a cavity of a cartridge that is rotated around a reciprocating carrier. The cartridges are affixed to a cylinder that's ten inches in length and eight and one half inches in circumference which is attached to an octagonal shaped drive shaft that rotates in one-eighth revolutions. The carrier is attached to a centered metal axis affixed to a timing gear from which a magnetic head derives the basic synchronization pulses for the carrier electronic driving circuits. Upon ROM command the carrier reciprocates along its axis until it's collected for samples from the selected cartridges. The carrier then moves to the blast zone where its content is spewed through a nose or mouth wand by a blast of air from a miniaturized pump. The cartridges are activated via a piezoelectric transducer of the extensional type in which motion is generated by applying voltage to the piezoelectric crystal in a radial direction. The invention is a peripheral PC device or standalone unit that allows its user to transmit and receive sensory transmissions; specifically, smell, taste and touch. The taste and smell functions allow the user to select premixed flavors and scents or mix and match flavors or scents by selecting coded characters that correspond to synthetic or natural flavors or scents. The texture features of the software allows the user to select predetermined fabric textures, such as wool cotton, silk, etc. The environmental features of the software allows the user to select various weather conditions such as air temperature, wind velocity, and so forth. Once the user makes the desired sensory selections he can then select, save, send or create from the file prompt. The SAVE selection allows the user to store the selected computations for future use. The SEND selection allows the user to send the computations to a receiving sense-simile machine via modem as follows.

Once the user inserts the desired phone number in the appropriate prompt and selects ENTER, a charge couples device converts the electric coded characters' corresponding light signals into an electric current received from its thousands of tiny cells. The varying voltages are then converted to digital signals for the modem to combine them with a carrier wave of electric current for sending along telephone lines. Once the electric current is received by the receiving unit's modem and demodulated, the decoded corresponding characters are fed to the receiving sense-simile machine via its CPU where it is stored or designated for creation. Once creation is selected, the creating unit's microprocessor uses the decoded characters, selects the corresponding blends and quantities transmitted by matching the characters with corresponding cartridges containing the appropriate substance thereby causing the designated cartridges on the appropriate cylinder to release a portion of its contents onto a nylon surface housed in a special tubing in the center of the cartridge. Using a miniature pressurized canister, the unit then disperses those flavors and/or fragrances from the tubing through the appropriate aperture producing the desired taste and/or fragrance sensation for the user.

The machine contains fine powdered or liquid synthetic, natural flavors and fragrances housed in corncob shaped cartridges that contain kernel shaped substance cartridges. It also contains two feel chambers to produce the desired physical sensations. The weather chamber contains pressurized cooling and heating agents as well as mist agents and a strobed laser light to simulate the desired weather conditions. The texture touch chamber contains a solid simulator, consistent of a conductive semi-permeable membrane acting as a substrate that conducts impulses to a conductive polymer fabric. The substrate and polymer syndesis conductivity transform the fabric structure to simulate the desired texture.

While the invention has been described with particular reference to the preferred embodiments, it will be understood by those skilled in the art that various changes may be made and equivalents may be substituted for elements of the preferred embodiments without departing from invention. For example, while the cylinder has been described as having eight rows of cartridges, other numbers of cartridges can be used when the cylinder revolutions are adjusted from eight steps per revolution to fit the number of rows.

As is evident from the foregoing description, certain aspects of the invention are not limited to the particular details of the examples illustrated, and it is therefore contemplated that other modifications and applications will occur to those skilled in the art. For example, the sense-simile machine functions can be incorporated into or housed in a personal computer and configured to work automatically. It is accordingly intended that the claims shall cover all such modifications and applications as do not depart from the true spirit and scope of the invention.

What is claimed is:

1. An apparatus, comprising:

a housing;

smell means in said housing for replicating desired smells;

taste means in said housing for replicating desired tastes;

texture means for simulating desired textures;

environmental means for simulating desired environmental conditions; and touch means for replicating desired feels, said touch means including:

a conductive polymer fiber having hair-like structures to stimulate nerves in human fingers, said conductive polymer fiber being positioned in said housing and accessible through a housing opening by human fingers;

a semi-permeable membrane, affixed to said conductive polymer fiber, acting as a substrate to conduct impulses to said conductive polymer fiber through a conductive syndesis region, said membrane and said syndesis region transforming said conductive polymer fiber to simulate a desired texture; and means for delivering a signal to said substrate to transform said conductive polymer fiber.

2. An apparatus, comprising:

a housing;

smell means in said housing for replicating desired smells;

taste means in said housing for replicating desired tastes;

touch means for replicating desired feels;

environmental means for simulating desired environmental conditions; and texture means for simulating desired textures, said texture means including:
- a cartridge mounted in said housing containing samples of fabrics on a spool, said samples of fabrics being accessible through a housing opening by a human hand;
- a lamp positioned to selectively illuminate said samples of fabrics;
- a colored lens adapted to rotate in front of said lamp to thereby selectively color said samples of fabrics;
- a clear lens in a second housing opening; and
- means for advancing fabric samples according to input information so that a desired fabric is visible through said clear lens.

3. An apparatus, comprising:

a housing;

smell means in said housing for replicating desired smells;

taste means in said housing for replicating desired tastes;

touch means for replicating desired feels;

texture means for simulating desired textures;

environmental means for simulating desired environmental conditions, said environmental means including:
- a cartridge mounted in aid housing;
- a heat source in said cartridge for producing heat in said housing;
- cooling means in said cartridge for producing a desired temperature in said housing;
- a capsule mounted in said cartridge having a liquid therein for producing humidity in said housing;
- a fan mounted in said housing for producing a flow of air to simulate wind velocity;
- a low power laser mounted in said housing; and
- a rotating lens having apertures positioned in front of said low power laser to simulate raindrops on a human hand.

4. An apparatus, comprising:

a housing having a first, second and third openings;

flavor means in said housing for replicating desired smells and tastes, said flavor means including a rotatable cylinder having a plurality of smell cartridges arranged in rows inside said cylinder and a plurality of taste cartridges arranged in rows inside said cylinder, said smell cartridges containing a smell substance and adapted to dispense a predetermined amount of said smell substance to a delivery system, said taste cartridges containing a taste substance and adapted to dispense a predetermined amount of said taste substance to a delivery system;

touch means for replicating a desired feel, said touch means including a conductive polymer fiber having hair-like structures to stimulate nerves in human fingers, a semi-permeable membrane, affixed to said conductive polymer fiber, acting as a substrate to conduct impulses to said conductive polymer fiber through a conductive syndesis region, said membrane and said syndesis region transforming said conductive polymer fiber to simulate a desired texture, said conductive polymer fiber being positioned in said housing and accessible through said first housing opening by human fingers;

texture means for simulating a desired texture, said texture means having a cartridge mounted in said housing containing samples of fabrics on a spool, a lamp positioned to selectively illuminate said samples of fabrics, a colored lenses adapted to rotate in front of said lamp to thereby selectively color said samples of fabrics, a clear lens in said second housing opening, said samples of fabrics being accessible through said third housing opening by a human hand; and environmental means for simulating desired environmental conditions, said environmental means having a cartridge mounted in said housing, a heat source in said cartridge for producing heat in said housing, cooling means in said cartridge for producing a desired temperature in said housing, a capsule mounted in said cartridge having a liquid therein for producing humidity in said housing, a fan mounted in said housing for producing a flow of air to simulate wind velocity, a low power laser mounted in said housing, and a rotating lens having apertures positioned in front of said low power laser to simulate raindrops on a human hand.

5. An apparatus, comprising:

a housing having a first, second and third openings;

smell means in said housing for replicating desired smells, said smell means including a rotatable smell cylinder having a plurality of smell cartridges arranged in rows inside said cylinder, said smell cartridges containing a smell substance and adapted to dispense a predetermined amount of said smell substance to a delivery system;

taste means in said housing for replicating desired tastes, said taste means including a rotatable taste cylinder having a plurality of taste cartridges arranged in rows inside said taste cylinder, said taste cartridges containing a taste substance and adapted to dispense a predetermined amount of said taste substance to a delivery system;

touch means for replicating a desired feel, said touch means including a conductive polymer fiber having hair-like structures to stimulate nerves in human fingers, a semi-permeable membrane, affixed to said conductive polymer fiber, acting as a substrate to conduct impulses to said conductive polymer fiber through a conductive syndesis region, said membrane and said syndesis region transforming said conductive polymer fiber to simulate a desired texture, said conductive polymer fiber being positioned in said housing and accessible through said first housing opening by human fingers;

texture means for simulating a desired texture, said texture means having a cartridge mounted in said housing containing samples of fabrics on a spool, a lamp positioned to selectively illuminate said samples of fabrics, a colored lenses adapted to rotate in front of said lamp to thereby selectively color said samples of fabrics, a clear lens in said second housing opening, said samples of fabrics being accessible through said third housing opening by a human hand; and environmental means for simulating desired environmental conditions, said environmental means having a cartridge mounted in said housing, a heat source in said cartridge for producing heat in said housing, cooling means in said cartridge for producing a desired temperature in said housing, a capsule mounted in said cartridge having a liquid therein for producing humidity in said housing, a fan mounted in said housing for producing a flow of air to simulate wind velocity, a low power laser mounted in said housing, and a rotating lens having apertures positioned in front of said low power laser to simulate raindrops on a human hand.

6. An apparatus for virtual transmission of desired smells and tastes, comprising:

transmission means for receiving input data representative of the desired smells and tastes to be virtually transmitted and producing an output signal representative of the smells and tastes to be virtually transmitted;

a housing;

a plurality of individual smell and taste substances releasably contained in said housing;

receiving means in said housing for receiving said output signal, controllably releasing measured amounts of said individual smell and taste substances in response to said output signal, and producing one of a smell, taste and flavor to replicate the desired smells and tastes.

7. An apparatus, as set forth in claim 6, including means for dispersing said smell and taste substances in a predetermined direction.

8. An apparatus, as set forth in claim 6, including means for signaling when any one of said smell and taste substances is depleted.

9. An apparatus replicating desired smells and tastes, comprising:

a housing;

a plurality of individual smell and taste substances releasably contained in said housing;

means in said housing for controllably releasing measured amounts of said individual smell and taste substances in response to receiving a signal representative of the desired smells and tastes, and producing one of a smell, taste and flavor to replicate the desired smells and tastes; and means for dispersing said smell and taste substances in a predetermined direction.

10. An apparatus, as set forth in claim 9, including means for signaling when any one of said smell and taste substances is depleted.

\* \* \* \* \*